(12) United States Patent
Russell et al.

(10) Patent No.: US 9,103,720 B2
(45) Date of Patent: Aug. 11, 2015

(54) METHODS FOR ASSAYING POLYMERS USING AN INTEGRATED COMPUTATIONAL ELEMENT

(71) Applicant: Halliburton Energy Services, Inc., Houston, TX (US)

(72) Inventors: Aaron Gene Russell, Humble, TX (US); Johanna Haggstrom, Kingwood, TX (US); Robert P. Freese, Pittsboro, NC (US)

(73) Assignee: Halliburton Energy Services, Inc., Houston, TX (US)

( * ) Notice: Subject to any disclaimer, the term of this patent is extended or adjusted under 35 U.S.C. 154(b) by 97 days.

(21) Appl. No.: 13/938,842

(22) Filed: Jul. 10, 2013

(65) Prior Publication Data

US 2015/0015884 A1 Jan. 15, 2015

(51) Int. Cl.
| | | |
|---|---|---|
| *G01J 3/46* | (2006.01) | |
| *G01J 3/28* | (2006.01) | |
| *G01J 3/36* | (2006.01) | |
| *G01N 21/31* | (2006.01) | |
| *C09K 8/035* | (2006.01) | |
| *E21B 49/08* | (2006.01) | |
| *G01J 3/12* | (2006.01) | |

(52) U.S. Cl.
CPC . *G01J 3/28* (2013.01); *C09K 8/035* (2013.01); *G01J 3/36* (2013.01); *G01N 21/31* (2013.01); *E21B 2049/085* (2013.01); *G01J 2003/1226* (2013.01)

(58) Field of Classification Search
CPC ............... G01J 3/46; G01J 3/50; G01J 3/51; G01J 3/524
USPC ..................................... 356/401–425
See application file for complete search history.

(56) References Cited

U.S. PATENT DOCUMENTS

| | | | |
|---|---|---|---|
| 6,198,531 B1 | 3/2001 | Myrick et al. | |
| 6,476,169 B1 | 11/2002 | Eoff et al. | |
| 6,529,276 B1 | 3/2003 | Myrick | |
| 6,790,671 B1 * | 9/2004 | Austin et al. | 436/172 |
| 7,123,844 B2 | 10/2006 | Myrick | |
| 7,834,999 B2 | 11/2010 | Myrick et al. | |
| 7,911,605 B2 | 3/2011 | Myrick et al. | |
| 7,920,258 B2 | 4/2011 | Myrick et al. | |
| 2008/0133193 A1 | 6/2008 | Gdanski et al. | |
| 2009/0073433 A1 | 3/2009 | Myrick et al. | |

(Continued)

FOREIGN PATENT DOCUMENTS

WO 2015006092 1/2015

OTHER PUBLICATIONS

International Search Report and Written Opinion for PCT/US2014/045012 dated Oct. 21, 2014.

*Primary Examiner* — Abdullahi Nur
(74) *Attorney, Agent, or Firm* — McDermott Will & Emery LLP; Craig W. Roddy

(57) ABSTRACT

Various molecular characteristics of a polymer may be determined using an integrated computational element to assay the polymer. Methods for assaying a polymer can comprise optically interacting electromagnetic radiation with a polymer and an integrated computational element; and determining a molecular characteristic of the polymer, using the integrated computational element. The molecular characteristic of the polymer may be used to determine a bulk characteristic of a fluid phase in which the polymer may be disposed.

24 Claims, 3 Drawing Sheets

(56) References Cited

U.S. PATENT DOCUMENTS

| | | |
|---|---|---|
| 2009/0182693 A1 | 7/2009 | Fulton et al. |
| 2009/0219538 A1 | 9/2009 | Myrick et al. |
| 2009/0219539 A1 | 9/2009 | Myrick et al. |
| 2010/0269579 A1 | 10/2010 | Lawrence et al. |
| 2012/0150451 A1 | 6/2012 | Skinner et al. |
| 2013/0031964 A1 | 2/2013 | Tunheim et al. |
| 2013/0031970 A1 | 2/2013 | Freese et al. |
| 2013/0031971 A1 | 2/2013 | Freese et al. |
| 2013/0031972 A1 | 2/2013 | Freese et al. |
| 2013/0032333 A1 | 2/2013 | Freese et al. |
| 2013/0032334 A1 | 2/2013 | Freese et al. |
| 2013/0032338 A1 | 2/2013 | Kalia et al. |
| 2013/0032339 A1 | 2/2013 | Kalia et al. |
| 2013/0032340 A1 | 2/2013 | Freese et al. |
| 2013/0032344 A1 | 2/2013 | Freese et al. |
| 2013/0032345 A1 | 2/2013 | Freese et al. |
| 2013/0032545 A1 | 2/2013 | Freese et al. |
| 2013/0032736 A1 | 2/2013 | Tunheim et al. |
| 2013/0033701 A1 | 2/2013 | Tunheim et al. |
| 2013/0033702 A1 | 2/2013 | Tunheim et al. |
| 2013/0034842 A1 | 2/2013 | Tunheim et al. |
| 2013/0035262 A1 | 2/2013 | Freese et al. |

* cited by examiner

METHODS FOR ASSAYING POLYMERS USING AN INTEGRATED COMPUTATIONAL ELEMENT

BACKGROUND

The present disclosure generally relates to methods for assaying polymers, and, more specifically, to methods for determining a molecular characteristic of a polymer using an integrated computational element.

The physical properties of various polymers can often be a determining factor as to whether a particular polymer can be used successfully in a given application. For example, polymer physical properties such as molecular weight and degree of crosslinking can dictate the viscosity of a fluid phase in which the polymer is disposed. Due to their molecular complexity and frequent batch-to-batch variability, it can sometimes be desirable to assay the physical properties of a polymer before its use in an application in order to ensure that the polymer is capable of performing as intended. The physical properties of a polymer may also be referred to herein as a "molecular characteristic" of the polymer. As used herein, the term "molecular characteristic" will refer to an observable physical property of a plurality of polymer molecules, where the physical property is determined by the polymer's molecular structure.

In the case of small molecules, which have well-defined molecular structures of finite size, physical property measurements can be carried out by various techniques, including both spectroscopic and laboratory analyses, in order to determine a substance's suitability for a particular use. Such analyses of small molecules can often be carried out rapidly.

Polymers, in contrast, are much more difficult to analyze due to their high and variable molecular weights and much more complicated molecular structures. Even though many polymers interact extensively with electromagnetic radiation, their complex molecular structures can make it very difficult to extract meaningful structural information from a conventional spectroscopic assay. Physical properties of polymers are most often assayed using non-spectroscopic laboratory analyses, many of which are fairly time consuming and only of limited accuracy. Although time consuming, these non-spectroscopic analytical techniques can be satisfactory in many cases, at least for purposes of characterizing a pristine polymer. However, when it is desired to know how a polymer is performing in an ongoing application (i.e., in the field), for example, these analytical techniques can sometimes be unsatisfactory. In many instances, physical property assays for polymers are performed with the polymer dispersed in a fluid phase, and colligative property measurements on the fluid phase may be used to determine a physical property of the polymer. For example, colligative property measurements may be used to determine a polymer's molecular weight. However, colligative property measurements usually require careful and time-consuming standardization protocols and the use of a high purity fluid phase. Hence, for field-derived polymer samples, particularly field-derived polymer samples obtained in a fluid phase, standard polymer analyses based upon colligative property measurements may be too slow or inaccurate to provide meaningful physical property information, or may simply not be possible to perform.

In addition to assaying the physical properties of a polymer during or following an application, it can also be desirable to measure the physical properties of a polymer during or following its synthesis. For example, it can be desirable to determine if a particular set of reaction conditions is producing or has produced a polymer having a desired set of physical properties (e.g., molecular weight, degree of crosslinking, degree of branching, crystallinity, and the like). As one of ordinary skill in the art will recognize, typical polymer reaction mixtures may be very complex and non-amenable to the common polymer characterization techniques discussed above. On the supply side, there can often be considerable batch-to-batch variability of polymers, even those obtained from the same manufacturer. Thus, for quality control purposes, it can be highly desirable to determine a polymer's physical properties before deployment in a given application.

Although certainly not limited to this field of use, polymers are often employed extensively in the oilfield services industry. As discussed previously, the physical properties of a polymer can heavily impact the polymer's performance in a given application, and oilfield applications are no exception. The issues encountered in the oilfield services industry in regard to the physical properties of polymers are considered to be representative of those encountered in other fields. Illustrative uses of polymers in oilfield applications can include, for example, as a viscosifying or gelling agent, a friction reducer, a sealant composition, a diverting agent, a scale inhibitor, a relative permeability modifier, or the like, in various treatment fluids. Treatment fluids and treatment operations are described in more detail below. In addition to their use in treatment fluids, polymers may comprise various parts of downhole tools.

A treatment operation or tool employing a polymer having an incorrect physical property may fail due to the polymer not being capable of functioning as intended in a subterranean formation. For example, a polymer having an incorrect physical property may not convey satisfactory properties to a treatment fluid in which it is disposed, and the treatment fluid may then not perform as intended during a treatment operation. As an illustrative example, the degree of crosslinking may dictate the effective performance lifetime of a polymer and/or lead to premature fluid breaking. As another illustrative example, a treatment fluid containing a polymer with an incorrect molecular weight may not have a suitable viscosity (a function of the polymer's molecular weight and/or degree of crosslinking), which can impact the treatment fluid's ability to carry proppant particulates, divert a fluid in a subterranean formation, and the like. Hence, it can be desirable to assay for the physical properties of a polymer before or while forming a treatment fluid therefrom, including "on-the-fly."

The problem of assaying for the physical properties of polymers in the oilfield is even more complicated during and following a treatment operation. Before performing a treatment operation, some delay in analyzing the physical properties of a polymer or a treatment fluid formed therefrom is at least tolerable, although not preferable. However, for assaying a polymer or a treatment fluid during or after a treatment operation, the issues are much more complicated and may be difficult or impossible to overcome by conventional polymer analyses. Downhole or post-production analysis of a polymer may be desirable to determine if a satisfactory break has occurred, for example. However, the complex nature of produced fluids and formation fluids can make such polymer analyses difficult or impossible to perform by conventional techniques. Even to the extent that a produced fluid can be sampled and further characterized, significant analytical delays may lead to analyses that are not representative of the polymer's physical properties while downhole. Downhole analyses can also be particularly difficult to perform due to the harsh nature of the subterranean environment.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, as will occur to one having ordinary skill in the art and the benefit of this disclosure.

DETAILED DESCRIPTION

Figure 1:
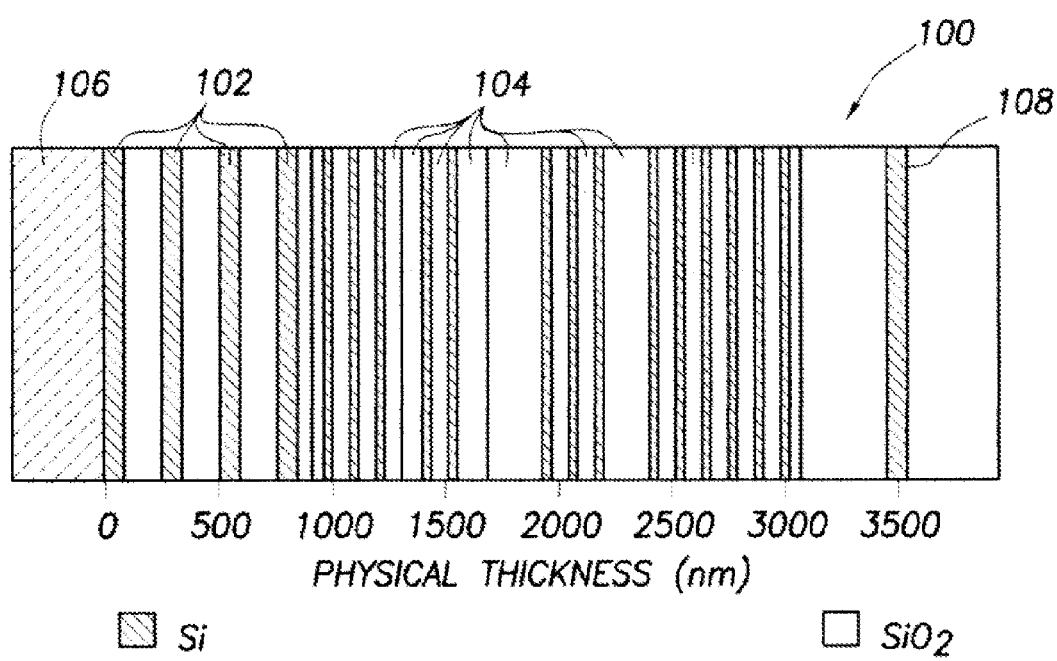
FIG. 1 shows a schematic of an illustrative integrated computational element (ICE).

The present disclosure generally relates to methods for assaying polymers, and, more specifically, to methods for determining a molecular characteristic of a polymer using an integrated computational element.

As described above, there may be several difficulties associated with conventional polymer analyses, and in many instances, these analyses may not be generally applicable or proceed rapidly enough to satisfy various types of process needs. Although spectroscopic analyses by themselves can typically be carried out relatively rapidly, the complex molecular structures of polymers can significantly limit one's ability to draw meaningful conclusions from the data. At best, conventional spectroscopic analyses are only able to draw rudimentary conclusions regarding the structure of a polymer (e.g., identity of functional groups, a rough estimate of the ratio of two monomers to one another, and the like), or its concentration in a fluid phase. However, it is not believed that conventional spectroscopic analyses have been used to any great extent to assay for one or more molecular characteristics of a polymer. Moreover, for polymer analyses conducted in field or process environments, including in the oilfield services industry, conventional spectroscopic instruments may be unsuitable due to their sensitive hardware and typical need for controlled analysis conditions.

In contrast to conventional analyses for determining the molecular characteristics of polymers (e.g., by colligative property measurements), which may be slow, necessarily performed in a fluid phase, and sensitive to the presence of interferents, the methods described herein may be performed much more rapidly on either solid or fluid samples with much less sensitivity to interference from other components that may be present. More specifically, the methods described herein utilize optical computing devices containing one or more integrated computational elements (ICE) in conjunction with analyzing one or more molecular characteristics of a polymer. Further disclosure regarding integrated computational elements and their advantages in this regard is presented below. The present inventors do not believe that there has been any prior contemplation in the art to utilize integrated computational elements in this manner. Each integrated computational element within an optical computing device can be specifically configured to analyze for a particular molecular characteristic of a given polymer type, even in the presence of interferents. Illustrative molecular characteristics of a polymer that may be analyzed by the methods described herein are not believed to be particularly limited and can include, for example, molecular weight, molecular weight distribution, degree of crosslinking, degree of branching, degree of substitution, uniformity of substitution, crystallinity, crystalline melting temperature, glass transition temperature, and any combination thereof.

Using one or more integrated computational elements for determining a molecular characteristic of a polymer may present a number of advantages. A leading advantage is that measurements made using an integrated computational element are much less sensitive to the presence of interferents than are other types of analyses, including conventional spectroscopic analyses, thereby allowing a polymer to be assayed under a much broader array of conditions than is otherwise typically possible. In this regard, the polymer may be analyzed substantially equivalently as either a solid or in a fluid state. Integrated computational elements and their associated hardware are also much more robust and less sensitive to corruption by field or process environments than are conventional spectroscopic instruments. Moreover, integrated computational elements and their associated hardware can produce extremely rapid analytical output, thereby making them suitable for determining the molecular characteristics of a polymer in real-time or near real-time. All of these features can prove advantageous when analyzing a polymer in a process or like environment.

As mentioned above, integrated computational elements may be used to analyze for one or more molecular characteristics of a polymer in the solid state. This feature may represent a particular advantage, since it can allow the polymer to be assayed while it is deployed in an application, without the need for removal of the polymer (i.e., of a part, vessel, seal or the like containing the polymer) and/or destructive sampling, thereby minimizing process downtime. By monitoring the molecular characteristics of a deployed solid polymer over time, one may be able to determine if a part, vessel, or seal has exceeded its useful lifetime and may be about to fail. Thus, using integrated computational elements in the manner described herein may allow an added measure of process safety to be realized.

Further advantages may be realized when the polymer is present in a fluid phase as well. Specifically, by assaying for the molecular characteristics of a polymer, a bulk characteristic of a fluid phase in which the polymer is disposed may be determined by extension. As used herein, the term "bulk characteristic" refers to a physical property of fluid phase in which a polymer is disposed, where the bulk characteristic is determined by a molecular characteristic of the polymer. For example, by knowing a polymer's molecular weight and/or degree of crosslinking (i.e., molecular characteristics), the viscosity (i.e., a bulk characteristic) of a treatment fluid in which the polymer is disposed may be readily determined, through techniques that will be evident to one having ordinary skill in the art.

From an operational standpoint, the methods described herein may be particularly advantageous, since they may allow intervention to take place in a process in which a polymer is being used, before an out-of-range molecular characteristic has the opportunity to manifest an unwanted process effect. By determining if a polymer has an out-of-range molecular characteristic before a treatment operation begins, for example, significant cost and time savings may be realized by not having to repeat a treatment operation and/or possibly remediate formation damage. For example, in some embodiments, a treatment fluid containing a polymer with a molecular weight that is too low may need to be further viscosified in some manner in order to attain a suitable working viscosity. Likewise, if the molecular weight is too high or if the degree of crosslinking is greater than expected, certain fluid breaking strategies may be more applicable than others. Furthermore, in some or other embodiments, the breaking of a treatment fluid may be followed using the methods described herein before, during or after a treatment operation. Premature breaking may be observed by assaying for a molecular characteristic of the polymer before conducting a treatment operation. Determining a molecular characteristic of a polymer during a treatment operation (e.g., in a subterranean formation) or after a treatment operation (e.g., in a produced fluid) may allow one to determine if an effective break has been achieved or is ongoing. For example, treatment fluid breaking may be determined by assaying for the degree of crosslinking of the polymer. These and other types of determinations are not readily performed by conventional polymer analyses, whereas they may be performed readily, in real-time or near real-time, using an integrated computational element, thereby allowing process control and feedback to take place. For example, in the event that an effective break has not been achieved, a different breaking strategy and/or a longer shut-in time may be used to decrease the molecular weight and crosslinking of the polymer.

One or more illustrative embodiments incorporating the disclosure herein are presented below. Not all features of an actual implementation are described or shown in this application for the sake of clarity. It is to be understood that in the development of an actual embodiment incorporating the present disclosure, numerous implementation-specific decisions must be made to achieve the developer's goals, such as compliance with system-related, business-related, government-related and other constraints, which vary by implementation and from time to time. While a developer's efforts might be complex and time-consuming, such efforts would be, nevertheless, a routine undertaking for one having ordinary skill in the art and the benefit of this disclosure.

The theory behind optical computing and a description of some conventional optical computing devices are provided in more detail in the following commonly owned United States patents and United States patent application Publications, each of which is incorporated herein by reference in its entirety: U.S. Pat. Nos. 6,198,531; 6,529,276; 7,123,844; 7,834,999; 7,911,605; 7,920,258; 2009/0219538; 2009/0219539; and 2009/0073433. Accordingly, the theory behind optical computing will not be discussed in any extensive detail herein unless needed to better describe one or more embodiments of the present disclosure. Unlike conventional spectroscopic instruments, which produce a spectrum needing further interpretation to obtain a result, the ultimate output of optical computing devices is a real number that can be correlated in some manner with a molecular characteristic of a polymer. For example, in the embodiments described herein, the optical computing device may output a real number that may be correlated with a polymer molecular weight or any other molecular characteristic noted above. The operational simplicity of optical computing devices allows them to rapidly produce an output, in real-time or near real-time, in some embodiments. Correlation of the numerical output may take place by comparing the numerical output of a polymer having an unknown molecular characteristic with the numerical output of a previously measured polymer having a known molecular characteristic.

In addition, significant benefits can sometimes be realized by combining the outputs from two or more integrated computational elements with one another, even when analyzing for a single molecular characteristic of interest. Specifically, in some instances, significantly increased detection accuracy may be realized. Techniques for combining the output of two or more integrated computational elements are described in commonly owned U.S. patent application Ser. Nos. 13/456,255; 13/456,264; 13/456,283; 13/456,302; 13/456,327; 13/456,350; 13/456,379; 13/456,405; and Ser. No. 13/456,443, each filed on Apr. 26, 2012 and incorporated herein by reference in its entirety. Any of the methods described herein may be carried out by combining the outputs of two or more integrated computational elements with one another. The integrated computational elements whose outputs are being combined may be associated or disassociated with the molecular characteristic of interest, display a positive or negative response when analyzing the molecular characteristic, or any combination thereof.

As alluded to above, the operational simplicity of optical computing devices makes them rugged and well suited for field or process environments, including deployment within a subterranean formation. Uses of conventional optical computing devices for analyzing fluids commonly encountered in the oil and gas industry, including while deployed within a subterranean formation, are described in commonly owned United States Patent Application Publications 2013/0031970, 2013/0031971, 2013/0031972, 2013/0032333, 2013/0032334, 2013/0032340, 2013/0032344, 2013/0032345 and 2013/0032545, each of which is incorporated herein by reference in its entirety.

As used herein, the term "polymer" refers to any high molecular weight compound in which a plurality of monomer units of one or more types are chemically bonded to one another. Polymers that may be assayed by the methods described herein are not believed to be particularly limited and can include both homopolymers and copolymers, either of which may be linear or branched. As used herein, the term "homopolymer" refers to a polymer containing a single type of repeating monomer unit. As used herein, the term "copolymer" refers to a polymer containing two or more types of monomer units. Copolymers may include random copolymers, block copolymers, graft copolymers and the like.

As used herein, the term "molecular weight" refers to any type of measurement used for characterizing the molar mass of a polymer. Illustrative molecular weight measurements suitable for characterizing the molar mass of a polymer may include, for example, the number average molecular weight ($M_n$), the weight average molecular weight ($M_w$), and the Z average molecular weight ($M_z$). The meaning of these terms will be familiar to one having ordinary skill in the art. Any of these molecular weight measurements may be representative of the degree of polymerization of the polymer. As used herein, the term "degree of polymerization" refers to the number of monomer units present within a polymer, which can be determined from the molecular weight.

As used herein, the term "molecular weight distribution" refers to the spread of molecular weight values in a plurality of polymer molecules of like type.

As used herein, the term "degree of substitution" refers to the number of side chain groups attached to the main chain of a polymer, usually expressed as the number of side chain groups per number of main chain monomer units.

As used herein, the term "uniformity of substitution" refers to the regularity with which side chain groups are attached to the main chain of a polymer.

As used herein, the term "degree of crosslinking" refers to the number of side chain groups forming intermolecular bonds with adjacent polymer molecules relative to the total number of side chain groups present on the main chain of the polymer.

As used herein, the term "degree of branching" refers to the extent to which the main polymer chain deviates from a linear polymer. The degree of branching may be expressed in terms of the number of branches per number of monomer units.

As used herein, the term "fluid" refers to any substance that is capable of flowing, including particulate solids, liquids, gases, slurries, emulsions, powders, muds, glasses, any combination thereof, and the like. In some embodiments, the fluid can comprise an aqueous fluid, including water, mixtures of water and water-miscible fluids, brine, and the like. In some embodiments, the fluid can comprise a non-aqueous fluid, including organic compounds (i.e., hydrocarbons, oil, a refined component of oil, petrochemical products, and the like). In some embodiments, the fluid can comprise a treatment fluid or a formation fluid.

As used herein, the term "formation fluid" refers to a fluid phase that natively occurs within a subterranean formation. Illustrative fluid phases that are found in a subterranean formation and which may be analyzed by the methods described herein to determine a molecular characteristic of a polymer include, for example, oil, liquid hydrocarbons, gaseous hydrocarbons, natural gas, reservoir brines, formation water, drilling muds, treatment fluids, any combination thereof, and the like.

As used herein, the term "treatment fluid" refers to a fluid that is placed in a location (e.g., a subterranean formation or a pipeline) in order to perform a desired function. Treatment fluids can be used in a variety of subterranean operations, including, but not limited to, drilling operations, production treatments, stimulation treatments, remedial treatments, fluid diversion operations, fracturing operations, secondary or tertiary enhanced oil recovery (EOR) operations, and the like. As used herein, the terms "treat," "treatment," "treating," and other grammatical equivalents thereof refer to any operation that uses a fluid in conjunction with performing a desired function and/or achieving a desired purpose. The terms "treat," "treatment," and "treating," as used herein, do not imply any particular action by the fluid or any particular component thereof unless otherwise specified. Treatment fluids for subterranean operations can include, for example, drilling fluids, fracturing fluids, acidizing fluids, conformance treatment fluids, damage control fluids, remediation fluids, scale removal and inhibition fluids, chemical floods, and the like. Any of these types of treatment fluids may contain a polymer.

As used herein, the term "produced fluid" refers to a fluid that is introduced to a subterranean formation and is subsequently obtained therefrom (i.e., produced from the subterranean formation) following a treatment operation.

As used herein, the terms "real-time" and "near real-time" refer to an output from an integrated computational element that is produced on substantially the same time scale as the optical interrogation of a substance with electromagnetic radiation. That is, a "real-time" or "near real-time" output does not take place offline after data acquisition and post-processing techniques. An output that is returned in "real-time" may be returned essentially instantaneously. A "near real-time" output may be returned after a brief delay, which may be associated with processing or data transmission time, or the like. It will be appreciated by one having ordinary skill in the art that the rate at which an output is received may be dependent upon the processing and data transmission rate.

As used herein, the term "electromagnetic radiation" refers to radio waves, microwave radiation, infrared and near-infrared radiation, visible light, ultraviolet radiation, X-ray radiation, and gamma ray radiation.

As used herein, the term "optically interact" and variants thereof refer to the reflection, transmission, scattering, diffraction, or absorption of electromagnetic radiation through or from a polymer or one or more integrated computational elements. Accordingly, optically interacted electromagnetic radiation refers to electromagnetic radiation that has been reflected, transmitted, scattered, diffracted, absorbed, emitted, or radiated from a polymer or an integrated computational element.

As used herein, the term "optical computing device" refers to an optical device that is configured to receive an input of electromagnetic radiation associated with a polymer and produce an output of electromagnetic radiation from a processing element arranged within the optical computing device. The electromagnetic radiation may optically interact with the polymer before or after optically interacting with the optical computing device. The processing element may be, for example, an integrated computational element (ICE), also known as a multivariate optical element (MOE) or an ICE CORE (Halliburton Energy Services), an illustrative example of which is described in more detail below. The electromagnetic radiation that optically interacts with the processing element may be changed so as to be readable by a detector, such that an output of the detector can be correlated to a molecular characteristic of the polymer. The output of electromagnetic radiation from the processing element can comprise reflected, transmitted, and/or dispersed electromagnetic radiation. Whether the detector analyzes reflected, transmitted, or dispersed electromagnetic radiation may be dictated by the structural parameters of the optical computing device as well as other considerations known to one having ordinary skill in the art. In addition, emission and/or scattering of the electromagnetic radiation, for example via fluorescence, luminescence, Raman, Mie, and/or Raleigh scattering, can also be monitored by the optical computing devices.

FIG. 1 shows a schematic of an illustrative integrated computational element (ICE) 100. As illustrated in FIG. 1, ICE 100 may include a plurality of alternating layers 102 and 104 of varying thicknesses disposed on optical substrate 106. In general, the materials forming layers 102 and 104 have indices of refraction that differ (i.e., one has a low index of refraction and the other has a high index of refraction), such as Si and $SiO_2$. Other suitable materials for layers 102 and 104 may include, but are not limited to, niobia and niobium, germanium and germania, MgF, and SiO. Additional pairs of materials having high and low indices of refraction can be envisioned by one having ordinary skill in the art, and the composition of layers 102 and 104 is not considered to be particularly limited. In some embodiments, the material within layers 102 and 104 can be doped, or two or more materials can be combined in a manner to achieve a desired optical response. In addition to solids, ICE 100 may also contain liquids (e.g., water) and/or gases, optionally in combination with solids, in order to produce a desired optical response. The material forming optical substrate 106 is not considered to be particularly limited and may comprise, for example, BK-7 optical glass, quartz, sapphire, silicon, germanium, zinc selenide, zinc sulfide, various polymers (e.g., polycarbonates, polymethylmethacrylate, polyvinylchloride, and the like), diamond, ceramics, and the like. Opposite to optical substrate 106, ICE 100 may include layer 108 that is generally exposed to the environment of the device or installation in which it is used.

The number, thickness, and spacing of layers 102 and 104 may be determined using a variety of approximation methods based upon a conventional spectroscopic measurement of a sample. These methods may include, for example, inverse Fourier transform (IFT) of the optical transmission spectrum and structuring ICE 100 as a physical representation of the IFT. The approximation methods convert the IFT into a structure based on known materials with constant refractive indices.

It should be understood that illustrative ICE 100 of FIG. 1 has been presented for purposes of illustration only. Thus, it is not implied that ICE 100 is predictive for any particular molecular characteristic of a given polymer. Furthermore, it is to be understood that layers 102 and 104 are not necessarily drawn to scale and should therefore not be considered as limiting of the present disclosure. Moreover, one having ordinary skill in the art will readily recognize that the materials comprising layers 102 and 104 may vary depending on factors such as, for example, the types of substances being analyzed and the ability to accurately conduct their analysis, cost of goods, and/or chemical compatibility issues.

The weightings that the layers 102 and 104 of ICE 100 apply at each wavelength are set to the regression weightings described with respect to a known equation, or data, or spectral signature. Briefly, ICE 100 may be configured to perform the dot product of the input electromagnetic radiation into ICE 100 and produce a desired loaded regression vector represented by each layer 102 and 104 for each wavelength. As a result, the output electromagnetic radiation intensity of the ICE 100 may be correlated to a molecular characteristic of a polymer. Further details regarding how ICE 100 is able to distinguish and process electromagnetic radiation are described in U.S. Pat. Nos. 6,198,531, 6,529,276, and 7,920,258, each of which was previously incorporated by reference.

It is to be recognized that the embodiments herein may be practiced with various blocks, modules, elements, components, methods and algorithms, which can be implemented through using computer hardware, software and combinations thereof. To illustrate this interchangeability of hardware and software, various illustrative blocks, modules, elements, components, methods and algorithms have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the spirit and scope of the embodiments expressly described.

Computer hardware used to implement the various illustrative blocks, modules, elements, components, methods and algorithms described herein can include a processor configured to execute one or more sequences of instructions, programming or code stored on a readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable PROM), registers, hard disks, removable disks, CD-ROMS, DVDs, or any other like suitable storage device.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and software.

As used herein, a machine-readable medium will refer to any non-transitory medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

Figure 2:
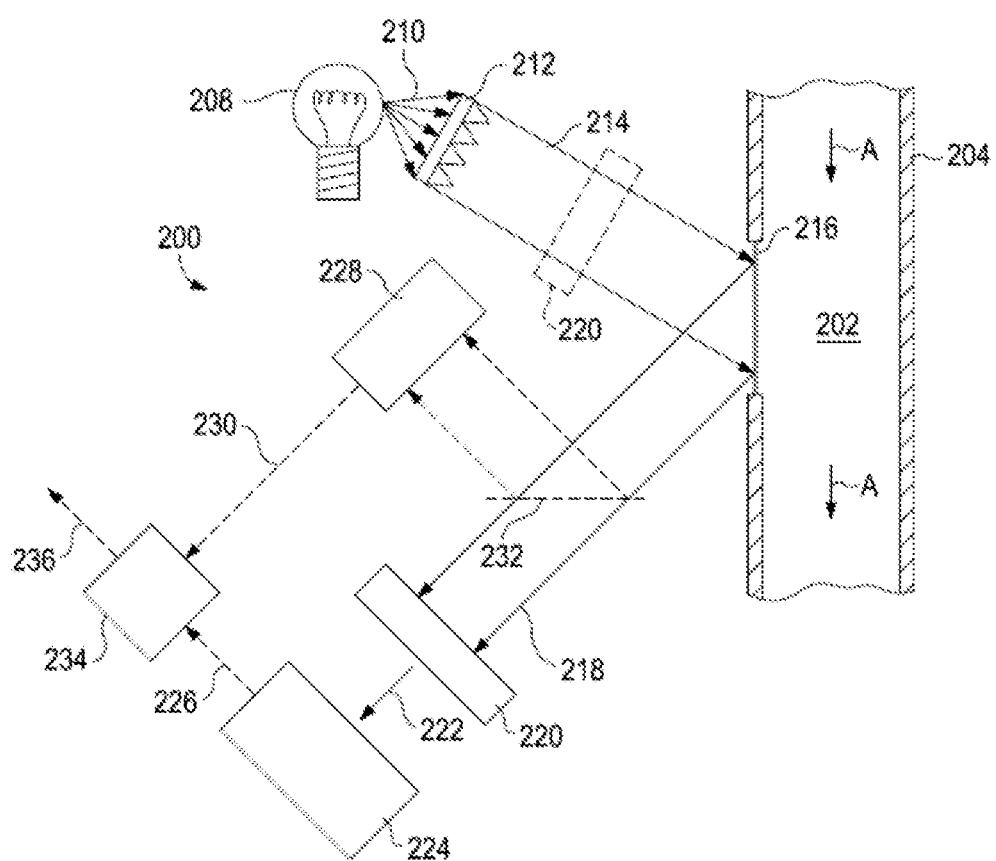
FIGS. 2 and 3 show schematics of illustrative optical computing devices employing an integrated computational element.
Figure 3:
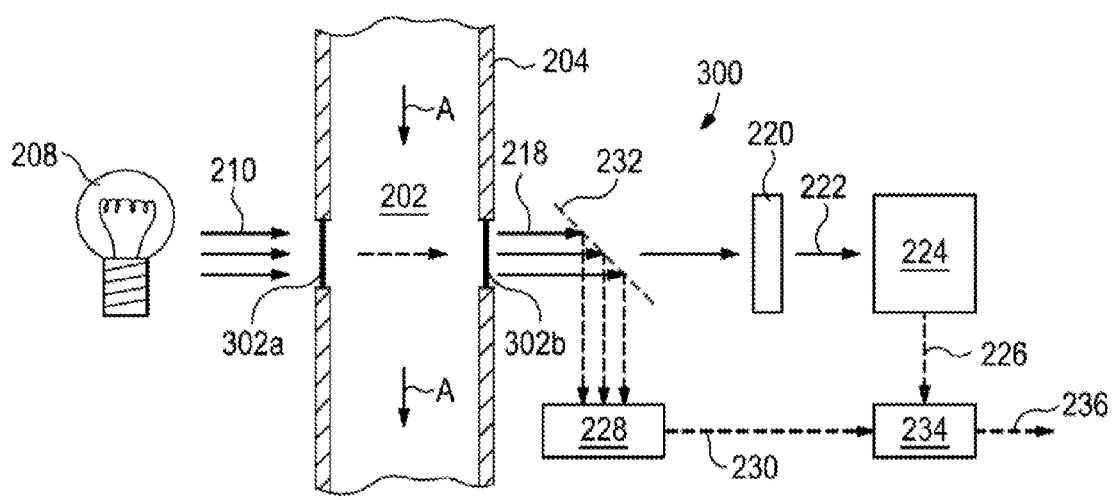

Illustrative configurations for optical computing devices containing a single integrated computation element will now be described. It is to be recognized that the device configurations depicted in FIGS. 2 and 3 are illustrative in nature only and can be modified extensively to accommodate the requirements of a particular analysis. As non-limiting examples, the single integrated computation elements of FIGS. 2 and 3 may be replaced by multiple integrated computational elements, the outputs of which may or may not be computationally combined with one another. In some embodiments, multiple integrated computational elements may be placed in series or parallel, or disposed on a movable assembly such that the electromagnetic radiation optically interacts with a different integrated computational element over time.

FIG. 2 shows an illustrative optical computing device 200 configured for monitoring fluid 202 by reflection, according to one or more embodiments. In the illustrated embodiment, fluid 202 may be contained or otherwise flowing within flow path 204. Flow path 204 may be a flow line, a pipeline, a wellbore, an annulus defined within a wellbore, or any flow lines or pipelines extending to/from a wellbore. Fluid 202 within flow path 204 may be flowing in the general direction indicated by the arrows A (i.e., from upstream to downstream). Portions of flow path 204 may be arranged substantially vertically, substantially horizontally, or any directional configuration therebetween, without departing from the scope of the disclosure.

Optical computing device 200 may be configured to determine a molecular characteristic of interest for a polymer within fluid 202, such as the polymer's molecular weight. Device 200 may include electromagnetic radiation source 208 configured to emit or otherwise generate electromagnetic radiation 210. Electromagnetic radiation source 208 may be any device capable of emitting or generating electromagnetic radiation, as defined herein. For example, electromagnetic radiation source 208 may be a light bulb, a light emitting diode (LED), a laser, a blackbody, a photonic crystal, an X-Ray source, any combination thereof, and the like. In some embodiments, lens 212 may be configured to collect or otherwise receive electromagnetic radiation 210 and direct beam 214 of electromagnetic radiation 210 toward fluid 202. Lens 212 may be any type of optical device configured to transmit or otherwise convey electromagnetic radiation 210 as desired, such as a normal lens, a Fresnel lens, a diffractive optical element, a holographic graphical element, a mirror (e.g., a focusing mirror), or a type of collimator. In some embodiments, lens 212 may be omitted from device 200 and electromagnetic radiation 210 may instead be directed toward fluid 202 directly from electromagnetic radiation source 208.

In some embodiments, device 200 may also include sampling window 216 arranged adjacent to or otherwise in contact with fluid 202 for detection purposes. Sampling window 216 may be made from a variety of transparent, rigid or semi-rigid materials that are configured to allow transmission of electromagnetic radiation 210 therethrough. For example, sampling window 216 may be made of glasses, plastics, semiconductors, crystalline materials, polycrystalline materials, hot or cold-pressed powders, any combination thereof, and the like. After passing through sampling window 216, electromagnetic radiation 210 impinges upon and optically interacts with fluid 202. As a result, optically interacted electromagnetic radiation 218 is generated by and reflected from fluid 202. It is to be recognized, however, that alternative configurations of device 200 may allow optically interacted electromagnetic radiation 218 to be generated by being transmitted, scattered, diffracted, absorbed, emitted, or re-radiated by and/or from fluid 202, without departing from the scope of this disclosure.

Optically interacted electromagnetic radiation 218 generated by the interaction with fluid 202 may be directed to or otherwise be received by ICE 220 arranged within the device 200. ICE 220 may be a spectral component substantially similar to ICE 100 described above with reference to FIG. 1. Accordingly, ICE 220 may be configured to receive the optically interacted electromagnetic radiation 218 and produce modified electromagnetic radiation 222 corresponding to a molecular characteristic of a polymer within fluid 202. In particular, modified electromagnetic radiation 222 is electromagnetic radiation that has optically interacted with ICE 220, whereby an approximation of the regression vector corresponding to the molecular characteristic of the polymer is obtained.

While FIG. 2 depicts ICE 220 as receiving reflected electromagnetic radiation from fluid 202, ICE 220 may be arranged at any point along the optical train of device 200, without departing from the scope of this disclosure. For example, in one or more embodiments, ICE 220 (as shown in dashed) may be arranged within the optical train prior to the sampling window 216 and while obtaining substantially the same results. In other embodiments, ICE 220 may generate modified electromagnetic radiation 222 through reflection, instead of transmission therethrough.

Modified electromagnetic radiation 222 generated by ICE 220 may subsequently be conveyed to detector 224 for quantification of the signal. Detector 224 may be any device capable of detecting electromagnetic radiation, and may be generally characterized as an optical transducer. In some embodiments, detector 224 may be, but is not limited to, a thermal detector such as a thermopile or photoacoustic detector, a semiconductor detector, a piezoelectric detector, a charge coupled device (CCD) detector, a video or array detector, a split detector, a photon detector (such as a photomultiplier tube), a photodiode, any combination thereof, and the like. Other detectors known to one having ordinary skill in the art may also be used.

In some embodiments, detector 224 may be configured to produce output signal 226 in real-time or near real-time in the form of a voltage (or current) that corresponds to a molecular characteristic of a polymer in fluid 202. The voltage returned by detector 224 is essentially the dot product of the optical interaction of optically interacted electromagnetic radiation 218 with ICE 220 as a function of the magnitude of the molecular characteristic of interest. As such, output signal 226 produced by detector 224 and the magnitude of the molecular characteristic may be related, such as directly proportional, for example. In other embodiments, however, the relationship may correspond to a polynomial function, an exponential function, a logarithmic function, and/or a combination thereof.

In some embodiments, device 200 may include second detector 228, which may be similar to first detector 224 in that it may be any device capable of detecting electromagnetic radiation. Second detector 228 may be used to detect radiating deviations stemming from electromagnetic radiation source 208. Undesirable radiating deviations can occur in the intensity of electromagnetic radiation 210 due to a wide variety of reasons and potentially cause various negative effects on device 200. These negative effects can be particularly detrimental for measurements taken over a period of time. In some embodiments, radiating deviations can occur as a result of a build-up of film or material on sampling window 216, which may have the effect of reducing the amount and quality of electromagnetic radiation ultimately reaching first detector 224. Without proper compensation, such radiating deviations may result in false readings that result in output signal 226 no longer being correlatable with the molecular characteristic of interest.

To compensate for radiating deviations, second detector 228 may be configured to generate compensating signal 230 that is generally indicative of the radiating deviations of electromagnetic radiation source 208, thereby normalizing output signal 226 generated by first detector 224. As illustrated, second detector 228 may be configured to receive a portion of optically interacted electromagnetic radiation 218 via beamsplitter 232 in order to detect the radiating deviations. In other embodiments, however, second detector 228 may be arranged to receive electromagnetic radiation from any portion of the optical train in device 200 in order to detect the radiating deviations, without departing from the scope of this disclosure.

In some embodiments, output signal 226 and compensating signal 230 may be conveyed to or otherwise received by signal processor 234 that is communicably coupled to both of detectors 224 and 228. Signal processor 234 may be a computer including a processor and a machine-readable storage medium having instructions stored thereon, which, when executed by signal processor 234, result in optical computing device 200 performing a number of operations, such as determining a molecular characteristic of interest of a polymer in fluid 202. Signal processor 234 may utilize an artificial neural network, such as those described in commonly owned United States Patent Application Publication 2009/0182693, which is incorporated herein by reference in its entirety. Signal processor 234 may also be configured to computationally combine the outputs of two or more integrated computational elements, if desired, for determining a molecular characteristic.

In real-time or near real-time, signal processor 234 may be configured to provide output signal 236 corresponding to a molecular characteristic of interest for a polymer in fluid 202, such as the polymer's molecular weight. Output signal 236 may be readable by an operator who can consider the results and make proper adjustments or take appropriate action, if needed. In some embodiments, output signal 236 may be conveyed, either wired or wirelessly, to an operator for consideration. In other embodiments, output signal 236 may be recognized by signal processor 234 as being within or outside a predetermined or preprogrammed range of suitable values for operation and may alert an operator in the event of an out-of-range value. In still other embodiments, signal processor 234 may autonomously undertake an appropriate corrective action in order to return output signal 236 to within a desired range.

FIG. 3 shows an illustrative optical computing device 300 configured for monitoring a fluid 202 by transmission, according to one or more embodiments. Optical computing device 300 may be similar in some respects to optical computing device 200 of FIG. 2, and therefore may be best understood with reference thereto, where like reference characters have been used to enumerate elements having similar functions. Unlike device 200, however, optical computing device 300 of FIG. 3 may be configured to transmit electromagnetic radiation 210 through fluid 202 via first sampling window 302a and second sampling window 302b arranged radially-opposite first sampling window 302a on flow path 204. First and second sampling windows 302a and 302b may be similar to sampling window 216 described above in FIG. 2 and therefore will not be described in detail again.

As electromagnetic radiation 210 passes through fluid 202 via first and second sampling windows 302a and 302b, it optically interacts with fluid 202, and optically interacted electromagnetic radiation 218 is subsequently directed to or is otherwise received by ICE 220. It is again noted that, ICE 220 may be arranged at any point along the optical train of the device 300, without departing from the scope of this disclosure. For example, in one or more embodiments, ICE 220 may be arranged within the optical train prior to first sampling window 302a. In yet other embodiments, ICE 220 may generate modified electromagnetic radiation 222 through reflection, instead of transmission therethrough.

Modified electromagnetic radiation 222 generated by ICE 220 is subsequently conveyed to detector 224 for quantification of the signal and generation of output signal 226, which corresponds to a molecular characteristic of interest for a polymer in fluid 202. Device 300 may also include second detector 228 for detecting radiating deviations stemming from electromagnetic radiation source 208. As illustrated, second detector 228 may be configured to receive a portion of the optically interacted electromagnetic radiation 218 via beamsplitter 232 in order to detect radiating deviations and produce compensating signal 230. Output signal 226 and compensating signal 230 may then be conveyed to or otherwise received by signal processor 234 to provide, in real-time or near real-time, output signal 236 that corresponds to a molecular characteristic of a polymer in fluid 202.

In some embodiments, methods described herein may comprise: optically interacting electromagnetic radiation with a polymer and an integrated computational element; and determining a molecular characteristic of the polymer, using the integrated computational element. In some embodiments, the methods may further comprise detecting the electromagnetic radiation that has optically interacted with the polymer and the integrated computational element; and generating an output signal based on the detected electromagnetic radiation, where the output signal is correlatable to the molecular characteristic of the polymer. In some embodiments, the output signal may provide a measure of the molecular characteristic of the polymer.

In some embodiments, the methods may further comprise providing the electromagnetic radiation that optically interacts with the polymer and the integrated computational element. In some embodiments, the electromagnetic radiation that optically interacts with the integrated computational element and the polymer may be provided from an external source such as a lamp, a laser, a light-emitting diode (LED), a blackbody, or the like. The type of electromagnetic radiation that is optically interacted with the polymer and the integrated computational element is not believed to be particularly limited. Suitable electromagnetic radiation sources may include visible light, infrared radiation, near-infrared radiation, ultraviolet radiation, X-ray radiation, gamma ray radiation, radio wave radiation, microwave radiation, any combination thereof, and the like. Particular types of electromagnetic radiation that optically interact strongly with the polymer may dictate the chosen type and specific wavelengths of electromagnetic radiation employed in the methods described herein.

In some embodiments, the electromagnetic radiation detected after optically interacting with the integrated computational element and the polymer may lie in the near-infrared region of the electromagnetic spectrum. In some embodiments, the detected electromagnetic radiation may lie within a wavelength range of about 1000 nm to about 5000 nm, or a range of about 1000 nm to about 4000 nm, or a range of about 1000 nm to about 3000 nm. Other detected wavelength ranges are possible and include, for example, detection in the radio wave region, the microwave radiation region, the infrared radiation region, the visible light region, the ultraviolet radiation region, the X-ray radiation region, the gamma ray radiation region, or any combination thereof. The particular detection region chosen will depend, at least in part, upon the nature of the optical interaction of the electromagnetic radiation with the particular polymer. Moreover, one of ordinary skill in the art will be able to choose a suitable detector for use in detecting a particular type of electromagnetic radiation.

Molecular characteristics of the polymer that may be determined using the methods described herein are not believed to be particularly limited. As alluded to above, molecular weight is one molecular characteristic of a polymer that may be particularly valuable for one of ordinary skill in the art to know with some precision. In addition to molecular weight, other molecular characteristics that may be determined using an integrated computational element according to the embodiments described herein include, for example, molecular weight distribution, degree of crosslinking, degree of branching, degree of substitution, uniformity of substitution, crystallinity, crystalline melting temperature, glass transition temperature, and any combination thereof. Some of these molecular characteristics may be derivable from one another. For example, by measuring crystallinity as a function of temperature, and perhaps other molecular characteristics, the crystalline melting temperature and glass transition temperature of a particular polymer may be determined. Given the benefit of the present disclosure and suitable reference standards to be used for developing a correlation function, one of ordinary skill in the art will be able to construct an integrated computational element configured for determining a particular molecular characteristic and utilizing the integrated computational element to determine a value for the molecular characteristic in a given polymer.

It is also believed that the polymers whose molecular characteristics may be determined by the methods described herein are not particularly limited. Although it is not believed that the identity of the polymer is limited in any way, particularly suitable polymers may include those utilized in the course of treating a subterranean formation. In this regard, the polymers of the description that follows should be considered illustrative of those that may be analyzed by the methods described herein. In some embodiments, the polymer may comprise a biopolymer, particularly a polysaccharide or a modified polysaccharide. Illustrative polysaccharides that may be analyzed by the methods described herein include, for example, a cellulose or modified cellulose, a guar or modified guar, a xanthan, a welan, a diutan, a scleroglucan, a succinoglycan, a chitosan, a chitin, a dextran, a starch, a sugar, any derivative thereof, or any combination thereof. Illustrative celluloses and modified celluloses that may be analyzed by the methods described herein include, for example, carboxymethylcellulose, carboxyethylcellulose, carboxymethylhydroxyethylcellulose, hydroxyethylcellulose, and the like. Illustrative guars and modified guars that may be analyzed by the methods described herein include, for example, hydroxypropylguar, carboxymethylhydroxypropylguar, carboxymethylguar, hydroxyethylguar, carboxymethylhydroxyethylguar, and the like. In some or other embodiments, a polyacrylamide, a polyacrylate, a partially hydrolyzed polyacrylamide, a polymethacylamide, a polymethacrylate, any derivative thereof, or any combination thereof may be analyzed by the methods described herein. Other polymers that may be analyzed by the methods described herein include, for example, polyesters, poly(orthoesters), polyanhydrides, polycarbonates, polyamides, polyphosphazenes, polyvinyl alcohol, 2-acrylamido-2-methyl propane sulfonate-containing polymers and copolymers, poly(vinyl pyrollidone), poly(diallyldimethylammonium chloride), poly(ethylene glycol), poly(ethylene oxide), polylysine, poly(vinylamine), poly(ethyleneimine), poly(lactic acid), poly(glycolic acid), poly(acrylic acid), poly(methacrylic acid), and the like.

The physical state in which the polymer is analyzed using the methods described herein is not believed to be particularly limited. In some embodiments, the polymer may be optically interacted as a solid phase with the electromagnetic radiation. In some or other embodiments, the polymer may be present in a fluid phase while optically interacting the electromagnetic radiation. The fluid phase is not believed to be particularly limited and may comprise an aqueous fluid phase in some embodiments and an organic fluid phase in other embodiments. In some embodiments, the polymer may be soluble in the fluid phase. In other embodiments, a solid polymer may be fluidly suspended in the fluid phase. One of ordinary skill in the art will recognize that a polymer may convey a bulk characteristic to a fluid phase in which it is present, whether the polymer is soluble in the fluid phase or simply suspended. For example, the molecular weight of the polymer, which may be determined by the polymer chain length and/or the degree of crosslinking, may influence the viscosity of a fluid phase in which it is disposed. In some embodiments, the methods described herein may further comprise determining a bulk characteristic of the fluid phase from a molecular characteristic of the polymer. In some embodiments, the bulk characteristic of the fluid phase may represent the viscosity of the fluid phase. In further embodiments, the molecular characteristic from which the bulk characteristic is determined may comprise a molecular weight of the polymer.

In some embodiments, a fluid phase in which the polymer is present may comprise a treatment fluid. In some embodiments, the methods described herein may further comprise introducing the treatment fluid into a subterranean formation.

In some embodiments, methods described herein may comprise: providing a treatment fluid comprising a polymer; optically interacting electromagnetic radiation with the polymer and an integrated computational element; determining a molecular characteristic of the polymer, using the integrated computational element; and introducing the treatment fluid into a subterranean formation.

In general, the type of treatment fluid containing the polymer is not believed to be particularly limited. In some embodiments, the treatment fluid may comprise a fracturing fluid. In further embodiments, a fracturing fluid may be introduced to a subterranean formation at or above a fracture gradient pressure of the subterranean formation.

In some embodiments, in addition to the polymer, a fracturing fluid may also comprise a plurality of proppant particulates. Proppant particulates are not particularly limited in size or composition and may include, for example, particulates comprising sand, bauxite, ceramic materials, glass materials, polymer materials, polytetrafluoroethylene materials, nut shell pieces, cured resinous particulates comprising nut shell pieces, seed shell pieces, cured resinous particulates comprising seed shell pieces, fruit pit pieces, cured resinous particulates comprising fruit pit pieces, wood, composite particulates, and combinations thereof. Suitable composite particulates may comprise a binder and a filler material wherein suitable filler materials include silica, alumina, fumed carbon, carbon black, graphite, mica, titanium dioxide, metasilicate, calcium silicate, kaolin, talc, zirconia, boron, fly ash, hollow glass microspheres, solid glass, and combinations thereof. One having ordinary skill in the art will understand suitable ranges for viscosity values of a fracturing fluid in order to transport a plurality of proppant particulates to a desired location within a wellbore. One having ordinary skill in the art will further recognize that a fracturing fluid may be viscosified by a polymer.

In some or other embodiments, the treatment fluid containing the polymer can be a treatment fluid used for conformance control. Such treatment fluids can be used to form a fluid seal within the subterranean formation in order to block or substantially divert the flow of a fluid therein. In some or other embodiments, the polymer may comprise a relative permeability modifier, which may differentially restrict the passage of aqueous fluids in the subterranean formation in comparison to organic fluids. Relative permeability modifiers can include both hydrophobically modified hydrophilic polymers and hydrophilically modified hydrophilic polymers, such as those described in commonly owned U.S. Pat. No. 6,476,169, which is incorporated herein by reference in its entirety. Other illustrative uses of treatment fluids containing polymers include, for example, friction-reducing fluids, chelating fluids, scale inhibition fluids, and the like.

The analysis location for a polymer to be included in a treatment fluid is not believed to be particularly limited in the embodiments described herein. Depending on whether one needs to monitor a molecular characteristic of a polymer before or during a treatment operation, or whether one needs to proactively or reactively address an out-of-range molecular characteristic will determine the location(s) at which the polymer may be most effectively assayed using the integrated computational element.

In some embodiments, optically interacting electromagnetic radiation with the polymer and the integrated computational element may take place before the treatment fluid is introduced into the subterranean formation. Analyzing for a molecular characteristic of the polymer in this manner may serve as a measure of quality control and allow one to determine if the treatment fluid will have suitable properties for performing a treatment operation. In some embodiments, the molecular characteristic of the polymer may be determined before the polymer is placed in the treatment fluid. That is, in some embodiments, optically interacting electromagnetic radiation with the polymer and the integrated computational element may take place before the polymer is placed in a fluid phase to form the treatment fluid. In some embodiments, optically interacting electromagnetic radiation with the polymer and the integrated computational element may take place while synthesizing the polymer, thereby providing synthesis process feedback to an operator. In other embodiments, a polymer obtained from a supplier or other source may be optically interacted with electromagnetic radiation in order to determine a molecular characteristic thereof, using an integrated computational element. Initial analysis of the polymer in either manner, before its incorporation in a treatment fluid, may allow one to avoid having to adjust the treatment fluid's properties after its formulation, which may be somewhat complicated. Alternatively, in other embodiments, the molecular characteristic of the polymer may be determined after the treatment fluid is formulated, but before it is introduced into the subterranean formation. If needed, the methods described herein may further comprise altering a bulk characteristic of the treatment fluid, after determining the molecular characteristic of the polymer. One of ordinary skill in the art will understand how to adjust a bulk characteristic (i.e., property) of a treatment fluid in order to respond to an out-of-range molecular characteristic or an out-of-range bulk characteristic.

In some or other embodiments, optically interacting electromagnetic radiation with the polymer and the integrated computational element may take place while the treatment fluid is in the subterranean formation. Analyzing for a molecular characteristic of the polymer in this manner may allow one to determine how the polymer or a treatment fluid formed therefrom is performing while downhole. For example, in some embodiments, one may determine if a polymer is degraded by conditions being encountered in the subterranean formation. Conditions that may degrade a polymer while downhole include, for example, formation temperatures, reactive components that may be present in a subterranean formation (e.g., hydrogen sulfide), and the like. Such degradation may involve chain breaking to reduce the molecular weight, breaking of crosslinks, unwanted reaction with a component that is present in the formation, and the like, any of which can make the polymer unsuitable for its intended purpose. However, in some embodiments, degradation in the foregoing manner may be desirable, since it can lead to breaking of the viscosity of a treatment fluid. In other embodiments, a breaker may be added to the subterranean formation in order to achieve a satisfactory break, where the breaker may affect a molecular characteristic of the polymer. Suitable breakers in this regard may include, for example, acids, oxidizers, enzymes, and the like. Regardless of the manner in which breaking may take place, the methods described herein may be used to determine if a satisfactory break has taken occurred. In the event that a satisfactory break has not taken place, corrective actions may be undertaken. Suitable corrective actions that may be undertaken to address the failure of a treatment fluid to break include, for example, increasing the shut-in time, adding more breaker, adding a different breaker, or any combination thereof.

When utilized for analyzing a polymer within a subterranean formation, one or more integrated computational elements may be present in a fixed location within the subterranean formation, or they may be movable. In some embodiments, optical computing devices employing integrated computational element(s) may be affixed at one or more locations within the subterranean formation (e.g., on tubulars). In other embodiments, optical computing devices employing integrated computational element(s) may be removably placed at one or more locations within the subterranean formation, such as through wireline deployment, for example. In related embodiments, optical computing devices employing integrated computational element(s) may be located external to the subterranean formation but be in optical communication therewith by way of an optical fiber or like electromagnetic radiation conduit extending into the subterranean formation. In either case, the integrated computational element(s) may receive electromagnetic radiation from one or more points of interest within the subterranean formation in order to determine a molecular characteristic of a polymer therein.

In some embodiments, optically interacting electromagnetic radiation with the polymer and the integrated computational element may take place while producing the treatment fluid from the subterranean formation. Like the above embodiments in which the polymer is analyzed while in the subterranean formation, determining a molecular characteristic of the polymer following its production from the subterranean formation may allow one to determine if the polymer has performed as intended while downhole. For example, excessive molecular weight reduction may be indicative of polymer degradation in the subterranean formation, which may have resulted in a failed or not wholly successful treatment operation. However, a low polymer molecular weight may also be indicative of a successful break, if that is what is desired. Conversely, a polymer molecular weight that is too high may be indicative of an incomplete break.

In some embodiments, methods described herein may comprise: providing a treatment fluid comprising a polymer; introducing the treatment fluid into a subterranean formation; interacting the treatment fluid with the subterranean formation during a shut-in period; after the shut-in period, producing the treatment fluid from the subterranean formation; optically interacting electromagnetic radiation with the polymer in the produced treatment fluid and an integrated computational element; and determining a molecular characteristic of the polymer, using the integrated computational element.

In some embodiments, interacting the treatment fluid with the subterranean formation may comprise at least partially permeating the treatment fluid into the formation matrix surrounding a wellbore. In some embodiments, a desired effect of the treatment fluid on the subterranean formation may occur while interacting the treatment fluid with the subterranean formation.

When determining a molecular characteristic of a polymer in a produced treatment fluid, the methods described herein may further comprise determining a molecular characteristic of the polymer before its introduction to the subterranean formation, as generally described above. That is, in some embodiments, methods described herein may further comprise optically interacting electromagnetic radiation with the polymer and an integrated computational element, before introducing the treatment fluid into the subterranean formation; and determining a pre-treatment molecular characteristic of the polymer, using the integrated computational element. The pre-treatment molecular characteristic being determined may be the same as the post-treatment molecular characteristic being determined in the produced fluid, or the molecular characteristics may be different. Thus, in some embodiments, the methods described herein may further comprise calculating a change in a value of the molecular characteristic while the polymer has been in the subterranean formation. By having both pre-treatment and post-treatment values for a molecular characteristic of the polymer, one may more accurately determine if a treatment operation performed therewith has had a desired effect. In some embodiments, this may involve calculating a break time for the treatment fluid from the molecular characteristic of the polymer.

It is to be recognized that other than polymers, various additional components may be present in the treatment fluids and other compositions described herein. Illustrative components that can be present in any of the treatment fluids described herein include, for example, acids, acid-generating compounds, bases, base-generating compounds, surfactants, scale inhibitors, corrosion inhibitors, gelling agents, crosslinking agents, anti-sludging agents, foaming agents, defoaming agents, antifoam agents, emulsifying agents, de-emulsifying agents, iron control agents, proppants or other particulates, gravel, particulate diverters, salts, fluid loss control additives, gases, catalysts, clay control agents, chelating agents, corrosion inhibitors, dispersants, flocculants, scavengers (e.g., H₂S scavengers, CO₂ scavengers or O₂ scavengers), lubricants, breakers, delayed release breakers, friction reducers, bridging agents, viscosifiers, weighting agents, solubilizers, rheology control agents, viscosity modifiers, pH control agents (e.g., buffers), hydrate inhibitors, relative permeability modifiers, diverting agents, consolidating agents, fibrous materials, bactericides, tracers, probes, nanoparticles, any combination thereof, and the like. It is to be noted that, in some embodiments, any of the foregoing components may comprise a polymer. Any of these additional substances may also be detected and analyzed using an integrated computational element, if desired.

Embodiments disclosed herein include:

A. Methods for determining a molecular characteristic of a polymer. The methods include optically interacting electromagnetic radiation with a polymer and an integrated computational element; and determining a molecular characteristic of the polymer, using the integrated computational element.

B. Methods for determining a molecular characteristic of a polymer in a treatment fluid. The methods include providing a treatment fluid comprising a polymer; optically interacting electromagnetic radiation with the polymer and an integrated computational element; determining a molecular characteristic of the polymer, using the integrated computational element; and introducing the treatment fluid into a subterranean formation.

C. Methods for determining a molecular characteristic of a polymer in a treatment fluid. The methods include providing a treatment fluid comprising a polymer; introducing the treatment fluid into a subterranean formation; interacting the treatment fluid with the subterranean formation during a shut-in period; after the shut-in period, producing the treatment fluid from the subterranean formation; optically interacting electromagnetic radiation with the polymer in the produced treatment fluid and an integrated computational element; and determining a post-treatment molecular characteristic of the polymer, using the integrated computational element.

Each of embodiments A, B, and C may have one or more of the following additional elements in any combination:

Element 1: wherein the molecular characteristic of the polymer comprises a polymer property selected from the group consisting of molecular weight, molecular weight distribution, degree of crosslinking, degree of branching, degree of substitution, uniformity of substitution, crystallinity, crystalline melting temperature, glass transition temperature, and any combination thereof.

Element 2: wherein the polymer is optically interacted as a solid phase with the electromagnetic radiation.

Element 3: wherein the polymer is present in a fluid phase while optically interacting with the electromagnetic radiation.

Element 4: wherein the method further comprises determining a bulk characteristic of the fluid phase from the molecular characteristic of the polymer.

Element 5: wherein the method further comprises detecting the electromagnetic radiation that has optically interacted with the polymer and the integrated computational element; and generating an output signal based on the detected electromagnetic radiation, the output signal being correlatable to the molecular characteristic of the polymer.

Element 6: wherein optically interacting the electromagnetic radiation with the polymer and the integrated computational element takes place while synthesizing the polymer.

Element 7: wherein the fluid phase is a treatment fluid.

Element 8: wherein the method further comprises altering a bulk characteristic of the treatment fluid, before introducing the treatment fluid into a subterranean formation.

Element 9: wherein the bulk characteristic comprises a viscosity of the treatment fluid and the molecular characteristic comprises a molecular weight of the polymer.

Element 10: wherein the polymer comprises a substance selected from the group consisting of a polysaccharide, a modified polysaccharide, a polyacrylamide, a partially hydrolyzed polyacrylamide, a polyacrylate, a polyacrylic acid, a polyester, a poly(orthoester), a polyanhydride, a polycarbonate, a polyamide, a polyphosphazene, a relative permeability modifier polymer, a polyvinyl alcohol, a 2-acrylamido-2-methyl propane sulfonic acid-containing polymer, a poly(vinyl pyrrolidone), a poly(diallyldimethylammonium chloride), a poly(ethylene glycol), a poly(ethylene oxide), a polylysine, a poly(vinylamine), a poly(ethyleneimine), a poly(lactic acid), a poly(glycolic acid), any derivative thereof, and any combination thereof.

Element 11: wherein optically interacting electromagnetic radiation with the polymer and the integrated computational element takes place before the treatment fluid is introduced into the subterranean formation.

Element 12: wherein optically interacting electromagnetic radiation with the polymer and the integrated computational element takes place before the polymer is placed in the treatment fluid.

Element 13: wherein optically interacting electromagnetic radiation with the polymer and the integrated computational element takes place while the treatment fluid is in the subterranean formation.

Element 14: wherein optically interacting electromagnetic radiation with the polymer and the integrated computational element takes place while producing the treatment fluid from the subterranean formation.

Element 15: wherein the method further comprises optically interacting electromagnetic radiation with the polymer and an integrated computational element before introducing the treatment fluid into the subterranean formation; and determining a pre-treatment molecular characteristic of the polymer, using the integrated computational element.

Element 16: wherein the pre-treatment molecular characteristic and the post-treatment molecular characteristic represent the same molecular characteristic and the method further comprises calculating a change in a value of the molecular characteristic while the polymer has been in the subterranean formation.

Element 17: wherein the method further comprises calculating a break time of the treatment fluid from the molecular characteristic of the polymer.

Element 18: wherein the method further comprises introducing a breaker into the subterranean formation and the breaker affects a molecular characteristic of the polymer.

By way of non-limiting example, exemplary combinations applicable to A, B, C include:

Combination 1: The method of A in combination with elements 1 and 2.

Combination 2: The method of A in combination with elements 1 and 3.

Combination 3: The method of A, B or C in combination with elements 1 and 5.

Combination 4: The method of A in combination with elements 1, 3 and 4.

Combination 5: The method of A in combination with elements 1, 3 and 7.

Combination 6: The method of A in combination with elements 1, 3, 7 and 8.

Combination 7: The method of A, B or C in combination with elements 1 and 10.

Combination 8: The method of B or C in combination with elements 1 and 8.

Combination 9: The method of B or C in combination with elements 1 and 11.

Combination 10: The method of B or C in combination with elements 1 and 12.

Combination 11: The method of B or C in combination with elements 1 and 13.

Combination 12: The method of B or C in combination with elements 1 and 14.

Combination 13: The method of C in combination with elements 1 and 15.

Combination 14: The method of C in combination with elements 1, 15 and 16.

Combination 15: The method of C in combination with elements 1 and 17.

To facilitate a better understanding of the present disclosure, the following example of preferred or representative embodiments is given. In no way should the following example be read to limit, or to define, the scope of the disclosure.

EXAMPLES

Prophetic Example

The optical spectra of a set of polymer samples having a range of known molecular characteristics will be obtained. Next, a series of optical transmission interference regression vectors will be generated, and their performance will be optimized for accuracy, sensitivity and manufacturability by varying the number of layers, the thickness of layers, and/or the material indices of refraction within a design candidate by comparison to the optical spectra. Once one or more suitable design candidates have been identified, an ICE will be manufactured using thin-film or like deposition techniques. The detector output obtained from the ICE will then be calibrated against polymer samples having known values for molecular characteristics to obtain a standard calibration curve. By reading the detector output of an unknown sample, the value of a molecular characteristic will be determined using the calibration curve.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The embodiments illustratively described herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. When "comprising" is used in a claim, it is open-ended. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claim, each numerical parameter should at least be construed in light of the number of reported significant digits and by applying ordinary rounding techniques.

The invention claimed is:

1. A method comprising:
optically interacting electromagnetic radiation with a polymer and an integrated computational element, the integrated computational element comprising a plurality of alternating layers of varying thicknesses with differing refractive indices; and
determining a molecular characteristic of the polymer, using the integrated computational element;
wherein optically interacting the electromagnetic radiation with the polymer and the integrated computational element produces an approximation of a regression vector for the molecular characteristic of the polymer.

2. The method of claim 1, wherein the molecular characteristic of the polymer comprises a polymer property selected from the group consisting of molecular weight, molecular weight distribution, degree of crosslinking, degree of branching, degree of substitution, uniformity of substitution, crystallinity, crystalline melting temperature, glass transition temperature, and any combination thereof.

3. The method of claim 1, wherein the polymer is optically interacted as a solid phase with the electromagnetic radiation.

4. The method of claim 1, wherein the polymer is present in a fluid phase while optically interacting with the electromagnetic radiation.

5. The method of claim 4, further comprising:
determining a bulk characteristic of the fluid phase from the molecular characteristic of the polymer.

6. The method of claim 5, wherein the bulk characteristic comprises a viscosity of the fluid phase.

7. The method of claim 4, wherein the fluid phase comprises a treatment fluid.

8. The method of claim 1, further comprising:
detecting the electromagnetic radiation that has optically interacted with the polymer and the integrated computational element; and
generating an output signal based on the detected electromagnetic radiation, the output signal being correlatable to the molecular characteristic of the polymer.

9. The method of claim 1, wherein optically interacting the electromagnetic radiation with the polymer and the integrated computational element takes place while synthesizing the polymer.

10. A method comprising:
providing a treatment fluid comprising a polymer;
optically interacting electromagnetic radiation with the polymer and an integrated computational element, the integrated computational element comprising a plurality of alternating layers of varying thicknesses with differing refractive indices;
determining a molecular characteristic of the polymer, using the integrated computational element;
wherein optically interacting the electromagnetic radiation with the polymer and the integrated computational element produces an approximation of a regression vector for the molecular characteristic of the polymer; and
introducing the treatment fluid into a subterranean formation.

11. The method of claim 10, wherein the molecular characteristic of the polymer comprises a polymer property selected from the group consisting of molecular weight, molecular weight distribution, degree of crosslinking, degree of branching, degree of substitution, uniformity of substitution, crystallinity, crystalline melting temperature, glass transition temperature, and any combination thereof.

12. The method of claim 10, further comprising:
determining a bulk characteristic of the treatment fluid from the molecular characteristic of the polymer.

13. The method of claim 12, further comprising:
altering the bulk characteristic of the treatment fluid, before introducing the treatment fluid into the subterranean formation.

14. The method of claim 12, wherein the bulk characteristic comprises a viscosity of the treatment fluid and the molecular characteristic comprises a molecular weight of the polymer.

15. The method of claim 10, wherein the polymer comprises a substance selected from the group consisting of a polysaccharide, a modified polysaccharide, a polyacrylamide, a partially hydrolyzed polyacrylamide, a polyacrylate, a polyacrylic acid, a polyester, a poly(orthoester), a polyanhydride, a polycarbonate, a polyamide, a polyphosphazene, a relative permeability modifier polymer, a polyvinyl alcohol, a 2-acrylamido-2-methyl propane sulfonic acid-containing polymer, a poly(vinyl pyrrolidone), a poly(diallyldimethylammonium chloride), a poly(ethylene glycol), a poly(ethylene oxide), a polylysine, a poly(vinylamine), a poly(ethyleneimine), a poly(lactic acid), a poly(glycolic acid), any derivative thereof, and any combination thereof.

16. The method of claim 10, wherein optically interacting electromagnetic radiation with the polymer and the integrated computational element takes place before the treatment fluid is introduced into the subterranean formation.

17. The method of claim 16, wherein optically interacting electromagnetic radiation with the polymer and the integrated computational element takes place before the polymer is placed in the treatment fluid.

18. The method of claim 10, wherein optically interacting electromagnetic radiation with the polymer and the integrated computational element takes place while the treatment fluid is in the subterranean formation.

19. The method of claim 10, wherein optically interacting electromagnetic radiation with the polymer and the integrated computational element takes place while producing the treatment fluid from the subterranean formation.

20. A method comprising:
providing a treatment fluid comprising a polymer;
introducing the treatment fluid into a subterranean formation;
interacting the treatment fluid with the subterranean formation during a shut-in period;
after the shut-in period, producing the treatment fluid from the subterranean formation;
optically interacting electromagnetic radiation with the polymer in the produced treatment fluid and an integrated computational element the integrated computational element comprising a plurality of alternating layers of varying thicknesses with differing refractive indices; and
determining a post-treatment molecular characteristic of the polymer, using the integrated computational element;
wherein optically interacting the electromagnetic radiation with the polymer and the integrated computational element produces an approximation of a regression vector for the post-treatment molecular characteristic of the polymer.

21. The method of claim 20, further comprising:
optically interacting electromagnetic radiation with the polymer and an integrated computational element before introducing the treatment fluid into the subterranean formation, the integrated computational element comprising a plurality of alternating layers of varying thicknesses with differing refractive indices; and
determining a pre-treatment molecular characteristic of the polymer, using the integrated computational element;
wherein optically interacting the electromagnetic radiation with the polymer and the integrated computational element produces an approximation of a regression vector for the pre-treatment molecular characteristic of the polymer.

22. The method of claim 21, wherein the pre-treatment molecular characteristic and the post-treatment molecular characteristic represent the same molecular characteristic, the method further comprising:
calculating a change in a value of the molecular characteristic while the polymer has been in the subterranean formation.

23. The method of claim 20, further comprising:
calculating a break time of the treatment fluid from the molecular characteristic of the polymer.

24. The method of claim 23, further comprising:
introducing a breaker into the subterranean formation, the breaker affecting a molecular characteristic of the polymer.

* * * * *